United States Patent [19]

Hageman et al.

[11] Patent Number: 5,453,490
[45] Date of Patent: Sep. 26, 1995

[54] PRODUCTION OF RECOMBINANT HUMAN INTERLEUKIN-1 INHIBITOR

[75] Inventors: Robert Hageman; Stephen P. Eisenberg; David Dripps, all of Boulder; Ronald Evans, Louisville; Henryk Cudny; Robert C. Thompson, both of Boulder, all of Colo.

[73] Assignee: Synergen, Inc., Boulder, Colo.

[21] Appl. No.: 298,180

[22] Filed: Aug. 30, 1994

Related U.S. Application Data

[60] Continuation of Ser. No. 994,483, Dec. 21, 1992, abandoned, which is a division of Ser. No. 442,652, Nov. 29, 1989, abandoned.

[51] Int. Cl.$^6$ .......................... C07K 14/435; C07K 1/18; C07K 1/36
[52] U.S. Cl. .......................... 530/350; 530/414; 530/416; 435/69.1
[58] Field of Search .................................... 530/350, 414, 530/416; 435/69.1, 320.1; 536/23.5

[56] References Cited

U.S. PATENT DOCUMENTS 5,075,222  12/1991  Hannum et al. ...................... 435/69.1

FOREIGN PATENT DOCUMENTS 8901946  3/1989  WIPO.

OTHER PUBLICATIONS

DIALOG abstract, BIOSIS No.: 85016332, Takahashi, K. 1987. Med. J. Hiroshima Univ. 35(4):813–842.
Pharmacia, Mar. 1980, "Ion Exchange Chromatography: Principles and Methods", Pharmacia Fine Chemicals, Sweden, pp. 29–33.
Roberts et al., J. Exp. Med., 163:511–519 (1986).
Seckinger et al., J. Immunol., 139:1541–1545 (1987).
Helfman et al., Proc. Nat'l. Acad Sci. USA, 80:31–35 (1983).
Suggs et al., Proc. Nat'l. Acad. Sci. USA, 78:6613–6617 (1981).
Bories et al., Biochem. and Biophys. Res. Comm., 147:710–715 (1987).
Arend et al., J. Immunol., 134:3868–3875 (1985).
Hannum et al., Nature, 343:336–340 (1990).
Furutani et al., Nucleic Acids Res., 13:5869–5882 (1985).
Kramer et al., Cell, 30:599–606 (1982).
Seckinger et al., 18th Forum in Immunology, pp. 486–488 (1987).
Billingham et al., British J. Rheum., 24 (suppl. 1):25–28 (1985).
Pujol et al., Life Sciences, 41:1187–1198 (1987).
Tan et al., Australian and New Zealand Rheum Assoc., Abstract on p. 113 (1986).
Maniatis, Molecular Cloning, A Laboratory Manual, Cold Springs Harbor Laboratory, CSH, N.Y., pp. 229–246, 270–307, and 387–389 (1982).
Seckinger et al., J. Immunol., 139:1546–1549 (1987).
Rosenstreich et al., J. Exp. Med., 168:1767–1779 (1988).
Hannum et al., Nature, 343:336–340 (1990).
Pharmacia Fine Chemicals, "Ion Exchange Chromatography," Table of Contents and pp. 29–31, Rahms I. Lund, Mar. 1980–1.
Scott et al. Mar. 1987. Biotechnology Progress, 3(1):49–56.
Sofer et al. 1983. BioTechniques, Nov./Dec., pp. 198–203.
Alberto et al. 1983. Molecular Biology of the Cell, Garland Publishing, Inc., N.Y., pp. 165–196.
Flaschel et al. 1983. "Ultrafiltration for the Separation of Biocatalysts."; In: Advances in Biochemical Engineering/Biotechnology, Springer Verlag, pp. 74, 120 1nd 123.
Barak et al, 1986. Eur. J. Immunol. 16:1449–1452.
Sofer, G., 1984. Bio/Technology, Dec. Issue, pp. 1035–1038.
Pharmacia 1986 Ion Exchange Product Profile, #50–01–221, XMPP.

*Primary Examiner*—Keith C. Furman
*Attorney, Agent, or Firm*—Finnegan, Henderson, Farabow, Garrett & Dunner

[57] ABSTRACT

A method for the production of commercial quantities of highly purified interleukin-1 inhibitor (IL-1i) from a recombinant host is disclosed. A preferred recombinant *E. coli* host for use in this method is also disclosed.

9 Claims, 1 Drawing Sheet

FIG. 1

PRODUCTION OF RECOMBINANT HUMAN INTERLEUKIN-1 INHIBITOR

This application is a continuation of application Ser. No. 07/994,483, filed Dec. 21, 1992, now abandoned, which is a divisional of Ser. No. 07/442,652, filed Nov. 29, 1989, now abandoned.

BACKGROUND OF THE INVENTION

The recombinant-DNA field, many proteins have been prepared in the laboratory in an amount suitable for research purposes. However, even though techniques to produce research quantities of these proteins have been optimized, these laboratory production and purification processes are often inadequate to produce commercial quantities of the desired protein which is of a quality sufficient to be used as a human pharmaceutical.

In order to produce commercial quantities of a given protein of an appropriate quality, unique fermentation, isolation, and purification techniques are often required. Moreover, the combination of the techniques and the order in which they are practiced often affect the amount of the protein recovered and the purity of the final product.

As previously described in co-pending U.S. patent application Ser. Nos. 199,915, 238,713, 248,521 and 266,531, filed May 27, 1988, Aug. 31, 1988, Sep. 23, 1988, and Nov. 3, 1988, respectively, (now U.S. Pat. No. 5,075,222) a unique protein named human interleukin-1 inhibitor has been isolated. These applications, specifically incorporated herein by reference, also describe methods for producing recombinant human interleukin-1 inhibitor, hereinafter referred to as "IL-1i," in laboratory quantities in transformed organisms useful in laboratory methods. However, these methods did not result in production of commercial quantities of IL-1i of a quality suitable for administration to humans.

The present inventors have found certain combinations of fermentations, isolation, and purification techniques which are capable of producing commercial quantities of highly purified IL-1i. These methods are described in this application. As used herein, the term "commercial quantities" is intended to mean at least several to tens to hundreds of grams of highly purified product obtained from each 100 liters of fermentation broth. By "highly purified product" is meant a material of sufficient purity to be administered to humans. In a preferred embodiment, "highly purified product" has less than 5 E.U. per dose of endotoxin and less than 0.0025% contamination by *E. coli* protein.

SUMMARY OF THE INVENTION

It is an object of the present invention to provide a method for the production of commercial quantities of recombinant human interleukin-1 inhibitor. This object is achieved by the methods described herein.

In order to achieve these objects, an improved strain for the production of IL-1i is described herein. That strain, named SGE90, is capable of producing at least 50 grams of highly purified IL-1i per 100 liters of fermentation broth when used in the methods described herein.

One method which is preferred for production of commercial quantities of the highly purified IL-1i described herein includes the following steps:

(1) fermentation;
(2) cell processing, including:
 (a) cell recovery,
 (b) lysis, and
 (c) clarification of the lysates;
(3) a first ion exchange step;
(4) a second ion exchange step;
(5) the final processing steps including concentration and diafiltration.

A third ion exchange step may be optionally added to achieve even greater product purity.

In a preferred embodiment, the fermentation step is carried out in microorganisms, particularly *E. coli*, while the first ionic exchange step is conducted with a column filled with the cation exchange resin "S-SEPHAROSE". Also in the preferred embodiment, the second ion exchange step is conducted with a column filled with an anion exchange resin, preferably "Q-SEPHAROSE". If the optional third ion exchange step is added, a column filled with a cation exchange resin, preferably "S-SEPHAROSE", is used.

It is to be understood that both the foregoing general description and the following detailed description are exemplary and explanatory only, and are not restrictive of the invention as claimed. The accompanying drawings, which are incorporated in and constitute a part of this specification, illustrates various embodiments of the invention and, together with the description, serve to explain the principles of the invention.

DESCRIPTION OF THE PREFERRED EMBODIMENTS

Reference will now be made in detail to the presently preferred embodiments of the invention, which, together with the following examples, serve to explain the principles of the invention.

Certain abbreviations and trademarks are used throughout this specification. The generic terminology for those abbreviations and trademarks are as follows:

"S" represent the term "sulphonate";
"SP" represents the term "sulphopropyl";
"CM" represents the term "carboxymethyl";
"Q" represents the term "quaternary amino";
"DEAE" represents the term "diethylaminoethyl";
"SEPHAROSE" is generically defined as "cross-linked agarose-based particle matrix";
"SEPHADEX" is generically defined as "cross-linked dextran particle matrix"; and
"TOYOPEARL" is generically defined as "poly(methylacrylate)/DEAE modified particles".

As noted above, the present invention relates to a process for the production of commercial quantities of IL-1i. As used herein, the term "commercial quantities" is intended to mean that at least several to tens to hundreds of grams of highly purified product from each 100 liters of fermentation broth are produced.

As noted previously, one of the preferred methods for production of commercial quantities of IL-1i described herein includes the following steps:

(1) fermentation of *E. coli* comprising a plasmid containing a DNA encoding IL-1i;
(2) cell processing, including:

(a) cell recovery,
(b) lysis, and
(c) clarification of the lysates;
(3) a first ion exchange step;
(4) a second ion exchange step;
(5) the final processing steps including concentration and diafiltration.

An optional third ion exchange step may also be conducted. Such an optional step would be performed immediately after the second ion exchange step.

The fermentation and cell processing steps for use in *E. coli* contemplated in this invention include those routinely known to one of ordinary skill in the art. Preferred embodiments of these steps are set forth in the examples which follow. However, any comparable procedures may be inserted in the place of those preferred procedures set forth below.

The process for the production of commercial quantities of IL-1i utilizes a first ion exchange column. As noted previously, the preferred column (described in Example 2), is filled with cationic "S-SEPHAROSE" resin. Other interchangeable resins may also be used, including but not limited to resins such as SP-C25 "SEPHADEX, CM SEPHADE," "CM SEPHAROSE," or CM cellulose. A second ion exchange column is then used for further purification of the IL-1i. As noted above, in the preferred embodiment Q-Sepharose is used as an anion exchange resin in this column. In addition, other comparable resins including but not limited to resins such as "DEAE-SEPHAROSE," "Q-SEPHADEX," or DEAE-cellulose may be employed.

In one embodiment of the present invention, a third ion exchange step is included immediately after the second ion exchange step. In this optional third step, a cation exchange column is used. This column preferably contains "S-SEPHAROSE" resin, however other interchangeable resins may also be used. Such other resins include, but are not limited to, "SP25-SEPHADEX", "CM SEPHADEX", "CM SEPHAROSE", CM cellulose or "CM TOYOPEARL".

Following these steps, the final process steps are undertaken. These include a concentration step, if desired, and diafiltration of the IL-1i. The parameters of these steps are routinely known to those of ordinary skill in the art, in light of the teachings found in the examples which follow.

Important to the operation of this process is a suitable set of quantitative analytical tools to evaluate yield and purity.

As described in greater detail in the procedures in Example 4, the assays which have been developed for these purposes include a reverse phase HPLC (RP-HPLC) assay, an ion exchange HPLC (IE-HPLC), an SDS-PAGE assay, a size exclusion assay, a trypsin peptide map, and an assay for biological activity. When tested in the first four of these assays, the highly-purified IL-1i produced by the present methods is greater than 90% pure. Preferably, when tested in the IE-HPLC, the highly purified IL-1i is at least 98% pure for both Mono Q and Mono S columns. Preferably, when tested in the SDS-PAGE assay, the highly purified IL-1i is at least 99.5% pure, and is at least 98% pure when tested in size exclusion assay. The trypsin peptide map of the highly purified IL-1i matches the pattern theoretically expected. The highly purified IL-1i demonstrates inhibition of IL-1 in the bioassay.

The following examples are provided to illustrate certain preferred embodiment of the present invention. These examples are intended to be illustrative only and are not intended to limit the scope of the claims appended hereto. All references provided in these examples are specifically incorporated herein by reference.

EXAMPLE 1

1. Transfer of the IL-1i cDNA from a Lambda Phage to a Bluescript Plasmid Cloning Vector The lambda phage GT10-IL-1i-2a (ATCC #40488) was digested with EcoRI and the 1.7 kb fragment carrying the IL-1i cDNA was purified by gel electrophoresis. This fragment was ligated to EcoRI-digested Bluescript SKM13- (Stratagene), resulting in the plasmid BS-IL-1i#2.

2. Development of an IL-1i Expression Vector Using the "T7" System

A. Description of pT5T

The T7 expression vector used for IL-1i production is called pT5T. It is essentially the same as pJU1003 [Squires, et al., *J. Biol. Chem.* (1988) 31: 16297–16302], except that there is a short stretch of DNA between the unique Bgl2 site 5' to the T7 promoter and the ClaI site in the tetracycline resistance gene. The sequence of this DNA is:

```
ATCGATGATA AGCTGTCAAA CATGAGAATT GAGCTCCCCG GAGATCCTTA GCGAAAGCTA
ClaI

AGGATTTTTT TTAGATCT
                Bgl2
```

Figure 1:
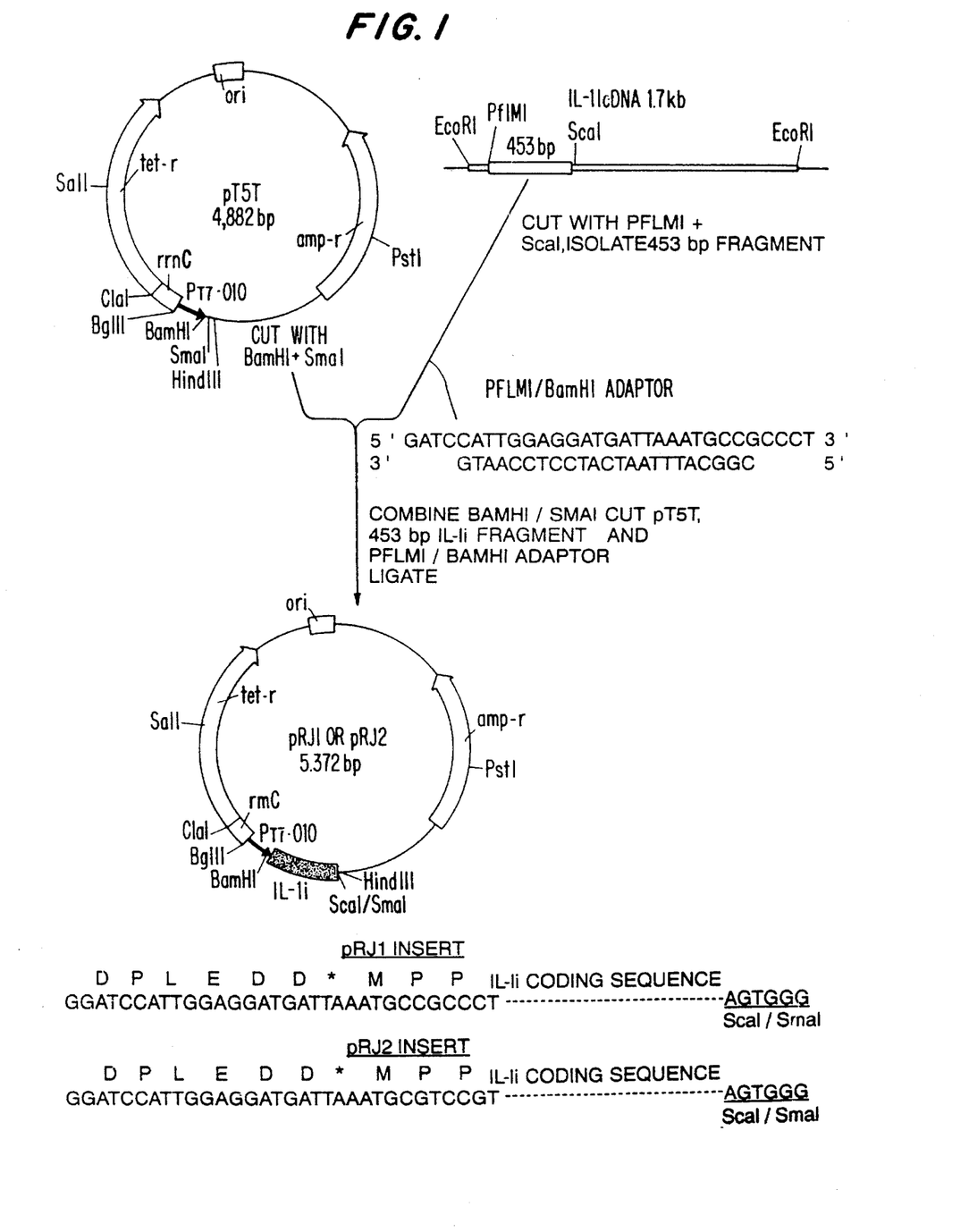
FIG. 1 depicts the construction of pRJ1 and pRJ2 as set forth in Example 1.

The vector was linearized with BamH1 and SmaI restriction enzymes. The plasmid BS-IL-1i#2 was digested with Pf1M1 and ScaI and the 453 bp fragment carrying the sequence coding for amino acids 4 to 152 of the mature IL-1i gene along with the termination codon and 3 bp of the 3' untranslated region was purified by polyacrylamide gel electrophoresis. Oligonucleotides with the sequences:

```
5'  GATCCATTGGAGGATGATTAAATGCCGCCCT  3'
5'          GTAACCTCCTACTAATTTACGGC          5'
``` were synthesized, phosphorylated at their 5' ends and annealed. These oligonucleotides contain sequences essential for the translational coupling of the T7 Φ10 gene to the IL-1i gene. A mixture containing the annealed oligonucleotides, the linearized vector fragment and the 453 bp IL-1i gene fragment was treated with T4 DNA ligase and then used to transform the *E. coli* strain JM109 (See FIG. 1).

B. Mutagenesis of IL-1i

Once a plasmid was isolated and shown to have the correct sequence, it was designated pRJ1. pRJ1 carries sequences coding for a variant of the IL-1i protein. The amino-terminal sequence of this variant is Met-Pro-Pro-Ser- . . . rather than Arg-Pro-Ser- . . . which is the aminoterminal sequence of the natural human protein. The aim here was to express a protein that is as close as possible to the natural protein, and that was done by mutagenizing the DNA coding for the IL-1i protein such that it codes for Met-Arg-Pro-Ser- . . . , as follows. The gene for IL-1i in pRJ1 was removed by digesting the plasmid at the unique BamH1 and Pst1 sites. The 1375 bp fragment was cloned between the BamH1 and Pst1 sites of M13 mp 19 and designated M13-IL-1i1. Oligonucleotide site directed mutagenesis was performed on isolated single stand DNA of M13IL-1i1 according to the procedure described in the BioRad Mutagene mutagenesis kit. The mutagenic oligonucleotide sequence is given below, along with the corresponding amino terminal amino acid sequence of the mutated IL-1i:

```
5'  TGATTAAATGCGTCCGTCTGGGAG  3'
         M   R   P   S   G   R
```

This mutagenesis produced M13IL-1i2 which differs from M13IL-1i1 in that the IL-1i protein encoded on this plasmid has the desired amino-terminal sequence and that the codons for Arg and Pro are those used preferably by *E. coli*.

C. Expression of IL-1i protein.

The mutagenized IL-1i gene was then transferred back into pT5T using the same procedure as described above. This second expression plasmid is designated pRJ2. pRJ2 was transformed into the *E. coli* strain BL21 (DE3) for expression. This strain [described in Studier and Moffat *J. Mol. Biol.* (1986) 189: 113–130] contains the T7 RNA polymerase gene under control of the IPTG inducible lac promoter on a nonexcisable lysogenic lambda bacteriophage. High level expression of rIL-1i was achieved by growing the cells [BL21(DE3)pRJ2] in Luria broth with 15 µg/ml tetracycline up to a cell density corresponding to an $A_{600}$ of 0.8. IPTG was added to a final concentration of 1.0 mM and the cells were allowed to grow for four hours. The cells were harvested by centrifugation and the rIL-1i was purified from the soluble cell lysate by standard protein chemistry techniques.

3. Development of an IL-1i Expression Vector Using the "tac promoter" System

A. Preparation of pDD1

The plasmid pJU 1003 (Squires, et al.) was cut with Hind3 and BamH1 and fused to a synthetic Human Pancreatic Secretory Trypsin Inhibitor (HPSTI) gene whose sequence is:

```
 EcorR1
GAATTCGATA  TCTCGTTGGA  GATATTCATG  ACGTATTTTG  GATGATAACG
CTTAAGCTAT  AGAGCAACCT  CTATAAGTAC  TGCATAAAAC  CTACTATTGC Pvu 1
AGGCGCAAAA  AATGAAAAAG  ACAGCTATCG  CGATCGCAGT  GGCACTGGCT
TCCGCGTTTT  TTACTTTTTC  TGTCGATAGC  GCTAGCGTCA  CCGTGACCGA GGTTTCGCTA  CCGTAGCGCA  GGCTGACTCT  CTGGGTCGTG  AAGCTAAGTG
CCAAAGCGAT  GGCATCGCGT  CCGACTGAGA  GACCCAGCAC  TTCGATTCAC CTACAACGAA  CTGAACGGTT  GCACTAAAAT  CTACAACCCG  GTATGTGGTA
GATGTTGCTT  GACTTGCCAA  CGTGATTTTA  GATGTTGGGC  CATACACCAT CCGACGGTGA  CACCTACCCG  AACGAATGCG  TGCTGTGCTT  CGAAAACCGT
GGCTGCCACT  GTGGATGGGC  TTGCTTACGC  ACGACACGAA  GCTTTTGGCA AAACGTCAGA  CCTCCATCCT  GATCCAGAAA  TCTGGTCCGT  GCTAAGTCGAC
TTTGCAGTCT  GGAGGTAGGA  CTAGGTCTTT  AGACCAGGCA  CGATTCAGCTG Hind 3
CCTGCAGAAG  CTT. . .
GGACGTCTTC  GAA. . .
``` by cutting the HPSTI gene with PvuI and Hind3 and ligating the PvuI/Hind3 fragment to the BamHI-Hind3 cut plasmid using a double stranded oligonucleotide adaptor with the sequence:

```
5'  GAT  CCG  ATC  TTG  GAG  GAT  GAT  TAA  ATG  AAA  AAG  ACC  GCT  ATC  GCC  AT  3'
3'       GC   TAG  AAC  CTC  CTA  CTA  ATT  TAC  TTT  TTC  TGG  CGA  TAG  CGG      5'
```

This synthetic HPSTI gene codes for a protein consisting of the signal (or leader) peptide for the *E. coli* ompA protein fused to the mature HPSTI protein. Thus, the purpose of this manipulation was to incorporate sequences coding for the ompA signal peptide into pJu 1003, for work described below. The resulting plasmid is pDD1. Plasmid pDD1 was digested with BstX1 and Hind3.

B. Construction of pDD3. Addition of *E. coli* translational signals to the IL-1i cDNA.

The plasmid pT5T (described above) was cut with BamH1 and SmaI. The plasmid BS-IL-1i#2 was cut with the PflM1 and ScaI, releasing a fragment 453 bp in length which codes for a portion of the IL-1i protein (see above). The BamH1/SmaI cut pT5T, the 453 bp IL-1i fragment, and an oligonucleotide adaptor with the sequence:

```
                BstX1
5' GA TCC ATC GCA GTG GCA CTG GGT GGT TTC GCT ACC GTA GCG
3'       G TAG CGT CAC CGT GAC CGA CCA AAG CGA TGG CAT CGC

CAG GCC CGT CCC T   3'
GTC CGG GCA G       5'
``` were fused to produce the plasmid pDD2. Plasmid pDD2 was cut with BstX1 and Hind3, releasing a 499 bp fragment which codes for all of the IL-1i protein and a portion of the ompA signal sequence. This 499 bp fragment was fused to BstX1/Hind3 cut pDD1, resulting in the plasmid pDD3.

C. Construction of pT3XI-2. Modification of pKK223-3

The starting plasmid for this construction was plasmid pKK223-3 purchased from Pharmacia. Plasmid pKK223-3 carries a partial gene for tetracycline resistance. This non-functional gene was replaced by a complete tetracycline resistance gene carried on plasmid pBR322. Plasmid pKK223-3 was digested completely with Sph1 and partially with BamH1. A 4.4 kilobase pair fragment was gel purified and combined with a synthetic adaptor with the sequence:

```
5'    GATCTAGAATTGTCATGTTTGACAGCTTATCAT      3'
3'        ATCTTAACAGTACAAACTGTCGAATAGTAGC    5'
``` and a 539 base pair fragment of DNA from a Cla1—Sph1 digest of the tetracycline resistance gene of pBR322 (PL Biochemicals, 27-4891-01). The resulting plasmid was designated pCJ1.

Next a Xhol linker purchased from New England Biolabs was inserted into plasmid pCJ1's PvuII site to form plasmid pCJX-1. This insertion disrupts the rop gene which controls plasmid copy number. An EcoR1 fragment containing the lacI gene was purified from plasmid pMC9 [Calos, et al., Proc. Natl. Acad. Sci. USA (1983), 80: 3015–3019] then inserted into the Xhol site with Xhol to EcoR1 adaptors having the sequence:

```
          5'  TCGAGTCTAGA       3'
          3'      CAGATCTTTTAA  5'
```

The polylinker sequence between the EcoR1 and Pst1 sites in plasmid pKK223-3 was next replaced with a polylinker sequence shown here:

The plasmid vector so obtained is designated pCJXI-1.

Finally, the tetracycline resistance gene was replaced with a similar gene which had the recognition sites for restriction enzymes Hind3, BamH1, and Sal1 destroyed by bisulfite mutagenesis. The following procedure was used to mutate the tetracycline resistance gene of pBR322. Plasmid pB322 was cut with Hind3, then mutagenized with sodium bisulfite [Shortle and Nathans, Proc. Natl. Acad. Sci. USA (1978) 5: 2170–2174)]. The mutagenzied DNA was ligated to form circular DNA, then cut with Hind3 to linearize any plasmid that escaped mutagenesis. E. coli JM109 [Yanish-Perron et al., Gene (1985) 33: 103–119] was transformed with the plasmid, then plated on selective media. Plasmids were isolated from tetracycline resistance colonies and checked for loss of the Hind3 site in the tetracycline resistance gene. The successfully mutated plasmid was designated pT1. A similar procedure was followed to mutagenzie the BamH1 site in pT1, yielding plasmid pT2. Plasmid pT2 in turn was mutagenized to remove the Sal1 site, forming plasmid pT3. A Cla1-BsmH1 fragment of pT3 carrying the mutated tetracycline resistance gene was isolated and used to replace the homologous fragment of pCJXI-1 to form pT3XI-2. The mutated tetracycline resistance gene still encodes a functional protein.

D. Formation of pT3XI-2-Φ10TC3FGFsyn. Preparing the tac promoter vector for IL-1i Initially a "gene" for basic Fibroblast Growth Factor (FGF) was synthesized. This "gene" codes for the same sequence as that reported for FGF by Sommer et al., but uses the codons that are found preferably in highly expressed genes in E. coli. The structure of this is such that the coding portion is preceded by a translational coupler sequence (see Squires, et al., 1988) to ensure efficient initiation of translation.

The FGF synthetic gene was first inserted into M13mp18 between the EcoR1 and Hind3 sites and sequenced. The structure of this gene is:

```
5'  AATTCCCGGGG  TACCAGATCT  GAGCTCACTA  GTCTGCA  3'
3'      GGGCCCC  ATGGTCTAGA  CTCGAGTGAT  CAG      5'
```

```
AATTCAGGA  TCCGATCGTG  GAGGATGATT  AAATGGGTAC  CATGGCTGCT  GGCTCCATCA
    GTCCT  AGGCTAGCAC  CTCCTACTAA  TTTACCCATG  GTACCGACGA  CCCAGGTAGT
EcoRI      BamHI       RBS                     FGFstart
           Transitional Coupler 3

CTACCCTGCC  GGCACTGCCG  GAAGACGGTG  GCTCCGGTGC  TTTCCCGCCG  GGCCACTTCA
GATGGGACGG  CCGTGACGGC  CTTCTGCCAC  CGAGGCCACG  AAAGGGCGGC  CCGGTGAAGT

AAGACCCGAA  ACGTCTGTAC  TGTAAAAACG  GTGGCTTCTT  CCTGCGTATC  CACCCGGATG
TTCTGGGCTT  TGCAGACATG  ACATTTTTGC  CACCGAAGAA  GGACGCATAG  GTGGGCCTAC

GTCGTGTCGA  CGGCGTACGT  GAAAAAAGCG  ACCCGCACA   TCAAACTGCA  GCTGCAGGCTG
CAGCACAGCT  TGCCGCATGC  ACTTTTTTCC  TGGGCGTGT   AGTTTGACGT  CGACGTCCGAC

AAGAACGTG   GTGTTGTATC  TATCAAAGGC  GTTTGCGCAA  ACCGTTACCT  GGCTATGAAAG
TTCTTGCAC   CACAACATAG  ATAGTTTCCG  CAAACGCGTT  TGGCAATGGA  CCGATACTTTC

AAGACGGTC   GTCTGCTGGC  TAGCAAATGT  GTAACTGACG  AATGTTTCTT  CTTCGAACGTC
TTCTGCCAG   CAGACGACCG  ATCGTTTACA  CATTGACTGC  TTACAAAGAA  GAAGCTTGCAG

TGGAAAGCA   ACAACTACAA  CACCTACCGT  TCTCGTAAAT  ACACTTCTTG  GTACGTTGCTC
ACCTTTCGT   TGTTGATGTT  GTGGATGGCA  AGAGCATTTA  TGTGAAGAAC  CATGCAACGAG

TGAAACGTA   CCGGCCAGTA  CAAACTGGGT  TCCAAAACTG  GCCCGGGTCA  GAAAGCAATCC
ACTTTGCAT   GGCCGGTCAT  GTTTGACCCA  AGGTTTTGAC  CGGGCCCAGT  CTTTCGTTAGG

TGTTCCTGC   CGATGAGCGC  TAAATCTTAA  ACTAGTA
ACAAGGACG   GCTACTCGCG  ATTTAGAATT  TGATCATTCGA
                            FGFstop         HinDIII
```

Relevant features of the gene are highlighted.

It was then isolated by digestion with BamH1 and Hind3 and inserted into BamH1/Hind3 cut pJU1003 (Squires, et al., 1988) yielding pJU1003-synFGF. This plasmid was cut with XbaI and Hind3 and the XbaI/Hind3 fragment carrying the FGF gene was isolated. This fragment was ligated into pT3X1-2 cut with EcoR1 and Hind3, using an EcoR1-XbaI linker:

```
5' pAAT  TCC  ACA  ACG  GTT  TCC  CT         3'
3'       GG   TGT  TGC  CAA  AGG  GAG  ATCp  5'
```

The new plasmid is designated pT3XI-2-Φ10TC3FGFsyn.

E. Formation of pDD4. Inserting IL-1i into a tac promoter vector pT3XI-2-Φ10TC3FGFsyn was cut with BamH1 and Hind3, which resulted in the linearization of the 7.4 kb expression vector and the release of the insert DNA. The DNA was then cut with NcoI and SmaI, which further fragmented the insert DNA. pDD3 was digested with BamH1 and Hind3 and the 546 bp IL-1i fragment was gel purified and fused with the BamH1/Hind3-cut pT3XI-2-Φ10TC3FGFsyn 7.4 kb vector DNA fragment, resulting in the plasmid pDD4.

F. Formation of pDD5. Use of E. coli preferred codons.

The plasmid pDD4 carries DNA coding for the ompA signal sequence and the full length of the IL-1i protein as it was derived from the original cDNA. Plasmid pDD4 was cut with BamH1 and Spe1, thus releasing a small fragment (170 bp) carrying the sequences for the ompA signal peptide and the codons for the first 29 amino acid residues of the IL-1i protein, and the large (7.8 kb) vector fragment. The large BamH1/Spe1 vector fragment was fused to two small fragments of DNA assembled from four synthetic oligonucleotides. The sequences of these fragments are:

```
5'  GAT  CCG  ATC  TTG  GAG  GAT  GAT  TAA  ATG  CGT  CCG  AGC  GGC  CGC
3'       GC   TAG  AAC  CTC  CTA  CTA  ATT  TAC  GCA  GGC  TCG  CCG  GCG

SacI
AAG  AGC  TCC  AAA  AT           3'
TTC  TCG  AGG  TTT  TAC  GTC  CG  5'

5' G  CAG  GCT  TTC  CGT  ATC  TGG  GAC  GTT  AAC  CAG  AAA  ACC  TTC  TAC
3'    A    AAG  GCA  TAG  ACC  CTG  CAA  TTG  GTC  TTT  TGG  AAG  ATG

CTG  CGC  AAC  AAC  CAA         3'
GAC  GCG  TTG  TTG  GTT  GAT  C  5'
```

These fragments carry sequences coding for the first 29 residues of the IL-1i protein using E. coli preferred codons [according to deBoer and Kastelein in *From Gene to Protein: Steps Dictating the Maximal Level for Gene Expression* (1986) Davis and Reznikoff, eds. pp. 225–283, Butterworths, N.Y.] and a unique SacI site after the sixth codon of IL-1i. The resulting plasmid is called pDD5.

G. Formation of pDD6. Changes to remove secondary structure in mRNA

Plasmid pDD5 was digested with BamH1 and SacI. The large (7.8 kb) Vector fragment resulting from this digestion was ligated to a synthetic fragment of DNA:

```
5' GAT CCG ATC TTG GAG GAT GAT TAA ATG CGA CCG TCC GGC CGT
3'         GC  TAG AAC CTC CTA CTA ATT TAC GCT GGC AGG CCG GCA

AAG AGC T   3'
TTC         5'
``` that codes for the first 6 residues of the IL-1i protein, but utilizes codons that prevent the formation of any hairpin loops near the 5' end of the mRNA, especially involving the "Shine-Dalgarno" sequence or the initiation codon for the IL-1i protein. This resulted in the formation of pDD6 which is the expression vector for production of IL-1i. Plasmid pDD6 was transformed into JM107 to yield the production strain SGE90.

EXAMPLE 2

1. Production of IL-1i from *E. coli* SGE90 Seed Growth

Ampules of a culture of SGE90 are prepared to be used for seed as follows. A culture streak is grown on Luria agar supplemented with 15 mg/l tetracycline HCl at 37° C. A single colony is picked and grown in Luria broth supplemented with 15 mg/l tetracycline HCl at 37° C. Growth is monitored by absorbance at 660 nm (henceforth referred to an OD). When the culture reaches about 1 OD it is aseptically centrifuged and resuspended in 20% glycerol:Luria broth (1:1). It is then distributed into ampules (1.5 ml per ampule) and stored at −70° C. Working stocks are made from this cell bank by growing one ampule in Luria broth supplemented with 15 mg/l tetracycline HCl to about 1 OD, then preparing ampules as above.

The fermentor used is prepared by thawing ampules in 40° C. tap water and inoculating 1 ml from the ampule prep into each of two 2 liter flasks containing 0.5 liter of Seed Media (Formula 1). The flasks are incubated for about 8 hours on a shaker at 37° C. at 350 rpm. The seed OD reaches about 3–4 by this time.

500 ml of the seed culture is used to inoculate 10 liters of Fermentation Media (Formula 2). This seed tank is then grown at 37° C. for 5–6 hours with pH control at 7.0, until the OD reaches approximately 5. The seed tank is then used to inoculate the fermentor.

2. Fermentation

The fermentation is carried out in 1600 liters of Fermentation Media (Formula 2). Temperature is controlled at 37° C. Dissolved oxygen is maintained at 30% (saturation with air at 3 psig). pH is controlled at 7.0 by the addition of HCl and NaOH as required.

Growth is monitored by OD. At approximately 10 OD synthesis of IL-1i is induced by the addition of Isopropyl-B-D-thiogalactoside (IPTG) to a final concentration of 150 uM. Fermentation is continued until the culture reaches an OD of about 40. Cell yield is about 150 kg solids per 1600 liters of fermentation media.

3. Cell Recovery and Washing

Cells are recovered using a desludging centrifuge (for example an Alfa Laval BTUX 510) and washed with 150 mM NaCl. Cells are resuspended to approximately 16% solids in 150 mM NaCl and then frozen and stored at −20° C.

4. Cell Rupture and Debris Removal

Fourteen kg of resuspended cells (about 2.2 kg solids) are thawed. EDTA is added to 5 mM and the cells lysed with two passes through a high pressure homogenizer. The pH is adjusted to 5.5 using 1M acetic acid. The lysate is diluted to 20±2 liters with water and clarified by centrifugation at 14,000× G for 20 minutes.

5. First Ion Exchange (a) Column Specifications. The column used is an Amicon G300×250 filled with 7.5 liter of "S-SEPHAROSE" resin (Pharmacia). All solutions are pumped through the column at 500 ml/min.

(b) Column Operation. The following buffer sequence is used for each cycle on the column. Buffer formulas are given in Example 4.

| Solution | Formula Number | Volume |
| --- | --- | --- |
| Equilibration | 3 | 20 l |
| Clarified Cell lysate |  | 15–25 l |
| Equilibration | 3 | 20 l |
| Salt Gradient Elution* | 3/4 | 40 l |
| NaOH Wash | 5 | 10 l |
| Acetic Acid Wash | 6 | 5 l |
| Storage | 7 | 20 l |

*Salt gradient is run from 150–400 mM NaCl.

*Salt gradient is run from 150–400 mM NaCl.

Eluate is collected by following the absorbance at 280 nm and collecting the peak eluting during the salt gradient. Recovery is about 55 g of IL-1i in about 10 l of the pooled fractions from 20 l of clarified cell lysate.

6. Second Ion Exchange (a) Diafiltration. The pooled eluate is concentrated if desired using a YM10 membrane (Amicon) and then the salt is removed by diafiltration using 4 volumes of Second ion exchange Equilibration buffer (Formula 8). A precipitate which forms at this step is removed by filtration through 3 uM and 0.22 uM filters.

(b) Column Specifications. The column used is an Amicon G180×250, filled with 5 liters of "Q-SEPHAROSE" (Pharmacia). All solutions are pumped through the columns at 350 ml/min.

(c) Column Operation. The following buffer sequence is used for each cycle on the column. Buffer formulas are given in Appendix A, following Example 3.

| Solution | Formula Number | Volume |
| --- | --- | --- |
| Equilibration | 8 | 20 l |
| Diafiltrate |  | 5–10 l |
| Equilibration | 8 | 20 l |
| Salt Gradient Elution* | 8/9 | 40 l |

| Solution | Formula Number | Volume |
|---|---|---|
| NaOH Wash | 5 | 10 l |
| Acetic Acid Wash | 6 | 5 l |
| Storage | 7 | 20 l |

*Salt gradient is run from 0 to 100 mm NaCl.

*Salt gradient is run from 0 to 100 mM NaCl.

Eluate is collected by following the absorbance at 280 nm and collecting the peak eluting during the salt gradient. Recovery is about 45 g of IL-1i in about 10 l of the pooled fractions from 7 l of Diafiltrate 1.

7. Final Processing (a) Concentration and Diafiltration. The pooled eluate from the second ion exchange column is concentrated to approximately 6 l using YM10 membrane (Amicon). The material is then diafiltered against 5 volumes of Diafiltration buffer (Formula 10). Final concentration then takes place to approximately 1–2 l, with a target concentration of 10–30 g/l. The precipitate which forms at this step is removed by filtration through 3 uM and 0.22 uM filters. The final concentrate is then filtered through a 0.22 uM filter into sterile, pyrogen free tubes and stored at −70° C. Recovery is about 80% from the pooled fractions from the second ion exchange column.

EXAMPLE 3

1. Removal of the N-terminal Methionine from *E. coli* produced IL-1i

IL-1i produced in *E. coli* has a sequence identical to that of IL-1i-x from human monocytes with the exception that the N-terminus has an additional methionine residue. This residue can be removed by incubating the inhibitor with the exoprotease Aminopeptidase 1 from *S. cerevisiae*.

10 mg of recombinant IL-1i (from the first S-Sepharose or the step of purification) is incubated with 1 mg of Yeast Aminopeptidase 1 purified as described by Change and Smith (J. Biol. Chem. 264, 6979, (1989)), in 50 mM ammonium carbonate pH 8.0 for 6 hours. The desmethionyl IL-1i is purified from the reaction mixture by further "S-SEPHAROSE" chromatography.

If wished, this step of the production process for desmethionyl can be avoided by expressing the IL-1i in an *E. coli* which contains the cDNA for yeast Aminopeptidase 1 enzyme in a suitable expression vector. This *E. coli* should also be unable to express the gene for Aminopeptidase P (Yoshimoto et al. *J. Biochem* (Tokyo) 104 93 (1988) since removal of the N-terminal methionine will otherwise lead to removal of the N-terminal arginine.

It will be apparent to those skilled in the art that various modifications and variations can be made in the processes of the present invention. Thus, it is intended that the present invention cover the modifications and variations of these processes provided they come within the scope of the appended claims and their equivalents.

A. Media and formula recipes

| Formula Number | Step | Name | Components | Conc. |
|---|---|---|---|---|
| 1 | Fermentation | Seed Medium | Yeast Extract | 5 g/l |
| | | | Tryptone | 10 g/l |
| | | | NaCl | 10 g/l |
| | | | Antifoam* | 0.2 ml/l |
| | | | Tetracycline | 15 mg/l |
| | | | DI Water | Q.S. |
| | | All ingredients except tetracycline are mixed and the pH adjusted to 7.5 with sodium hydroxide. Tetracycline is filter sterilized and added separately. | | |
| 2 | Fermentation | Fermentation Media | NZ Amine HD | 40 g/l |
| | | | $KH_2PO_4$ | 2 g/l |
| | | | $MgSO_4 \cdot 7H_2O$ | 1 g/l |
| | | | $NaSO_4$ | 6 g/l |
| | | | Sodium Citrate | 0.3 g/l |
| | | | Glycerol | 50 g/l |
| | | | Antifoam* | ca. 3 ml/l |
| | | | Trace minerals** | 4 ml/l |
| | | | Thiamine HCl | 10 mg/l |
| | | | Tetracycline HCl | 15 mg/l |
| | | | DI Water | Q.S. |
| | | All ingredients through antifoam are sterilized together. Trace minerals, | | |

-continued

| Formula Number | Step | Name | Components | Conc. |
|---|---|---|---|---|
| | | | thiamine and tetracycline are filter sterilized and added separately. *Added as needed. | |
| * | Fermentation | Antifoam | Macol 19 | 750 ml/l |
| | | | GE60 antifoam | 250 ml/l |
| ** | Fermentation | Trace Minerals | $FeCl_3 \cdot 6H_2O$ | 27 g/l |
| | | | $ZnCl_2$ | 1.3 g/l |
| | | | $CoCl_2 \cdot 6H_2O$ | 2 g/l |
| | | | $Na_2MoO_4 \cdot 6H_2O$ | 2 g/l |
| | | | $CaCl_2 \cdot 2H_2O$ | 2.5 g/l |
| | | | $CuCl_2 \cdot 2H_2O$ | 1.27 g/l |
| | | | $MnCl_2 \cdot 4H_2O$ | 3.3 g/l |
| | | | $H_3BO_3$ | 0.5 g/l |
| | | | HCl, conc. | 160 ml/l |
| | | | DI Water | Q.S. |
| 3 | First Ion Exchange | Equilibration | Sodium Acetate | 25 mM |
| | | | EDTA | 1 mM |
| | | | NaCl | 150 mM |
| | | | DI/UF Water | Q.S. |
| | | Adjust pH to 5.5 with 5M Acetic Acid. | | |
| 4 | First Ion Exchange | Elution/High Salt | Sodium Acetate | 25 mM |
| | | | EDTA | 1 mM |
| | | | NaCl | 400 mM |
| | | | DI/UF Water | Q.S. |
| | | Adjust pH to 5.5 with 5M Acetic Acid. | | |
| 5 | First/Second Ion Exchange | NAOH Wash | NAOH | 0.2 M |
| | | | NaCl | 1.0 M |
| | | | DI/UF Water | Q.S. |
| 6 | First/Second Ion Exchange | Acetic Acid Wash | Acetic Acid | 10 mM |
| | | | DI/UF Water | Q.S. |
| 7 | First/Second Ion Exchange | Storage | NaCl | 1 M |
| | | | DI/UF Water | Q.S. |
| 8 | Second Ion Exchange | Equilibration | Histidine | 20 mM |
| | | | EDTA | 1 mM |
| | | | DI/UF Water | Q.S. |
| | | Adjust pH to 6.0 using 5M HCl. | | |
| 9 | Second Ion Exchange | Elution/High Salt | Histidine | 20 mM |
| | | | EDTA | 1 mM |
| | | | NaCl | 100 mM |
| | | | DI/UF Water | Q.S. |
| | | Adjust pH to 6.0 using 5M HCl. | | |
| 10 | Diafiltration | Diafiltration | $NAH_2PO_4$ | 10 mM |
| | | | EDTA | 0.1 mM |
| | | | DI/UF Water | Q.S. |
| | | Adjust to pH 7.0 using 5M NAOH. | | |

| Time (min) | Percent B | Duration | |
|---|---|---|---|
| 0 | 0 | 5 | |
| 5 | 30 | 30 | (Start Gradient) |
| 35 | 50 | 40 | |
| 75 | 100 | 5 | (End Gradient) |
| 85 | 0 | 5 | |
| 95 | 0 | End | |

FLOW RATE:

1.0 ml/min

SAMPLE PREPARATION:

Dilute sample to 0.1–0.5 mg/ml with water.

INJECTION VOLUME:

100 ul

CHEMICALS:

| Chemical | Supplier | Cat. No. |
|---|---|---|
| TFA | Sigma | T-6508 |
| Acetonitrile, HPLC Grade | Baker | 9017-03 |

C.

MONO Q HPLC OF IL-1i

HPLC SYSTEM:

Beckman System Gold
    Programmable Sovent Module 126
    Scanning Detector Module 167
    Remote Interface Module
    HP Series 1050 Autosampler
    System Gold, Personal Chromatograph Software

COLUMN:

Pharmacia Mono Q HR 5/5

DETECTOR SETTINGS:
280 nm
MOBILE PHASE:
A: 20 mM TRIS, pH 7.5
B: 20 mM TRIS, pH 7.5+250 mM NaCl
GRADIENT CONDITIONS:
0% to 100% B in 60 minutes
FLOW RATE:
0.5 ml/min
SAMPLE PREPARATION:
None
INJECTION AMOUNT:
25 ug
D.

MONO S HPLC OF IL-1i

HPLC SYSTEM:
Beckman System Gold
 Programmable Solvent Module 126
 Scanning Detector Module 167
 Remote Interface Module
 HP Series 1050 Autosampler
 System Gold, Personal Chromatograph Software
COLUMN:
Pharmacia Mono S HR 5/5
DETECTOR SETTINGS:
280 nm
MOBILE PHASE:
A: 25 mM NaAc, pH 5.5+1 mM EDTA
B: 25 mM NaAc, pH 5.5+1 mM EDTA+500 mM NaCl
GRADIENT CONDITIONS:
0% to 60% B in 36 minutes.
FLOW RATE:
0.5 ml/min
SAMPLE PREPARATION
None
INJECTION AMOUNT:
25 ug
E.

SIZE EXCLUSION HPLC OF IL-1i

HPLC SYSTEM:
Beckman 114 Solvent Delivery Module
Beckman 165 Variable Wavelength Detector
Beckman System Gold Analog Interface Module 406
Beckman System Gold, Personal Chromatograph Software
COLUMN:
Bio-Sil TSK 250 (7.5 mm×30 cm)
DETECTOR SETTING:
280 mm
Range: 0–0.2 AU
MOBILE PHASE:
25 mM Na Acetate and 0.5M NaCl, pH 5.5
FLOW RATE:
0.5. mls/min
SAMPLE PREPARATION:
Dilute IL-1i solution with mobile phase to a final concentration of approximately 2 mg/ml
INJECTION VOLUME:
50 ul
F.

REDUCING SDS PAGE OF IL-1i

GEL PREPARATION:
Follow procedure outlined by Lammli in J. Mol. Biol., 80, 575–599 (1973).
SEPARATING GEL:

| | |
|---|---|
| Acrylamide | 15% |
| TRIS pH 8.8 | 375 mM |
| SDS | 0.1% |

STACKING GEL:

| | |
|---|---|
| Acrylamide pH 6.8 | 5% |
| SDS | 0.1% |

SAMPLE PREPARATION:
Sample is diluted 1:1 with Sample Buffer. The samples are then heated for 15 minutes at 65° C., spun and loaded onto the gel.

| | |
|---|---|
| TRIS pH 6.8 | 250 mM |
| SDS | 2.5% |
| 2-Mercaptoethanol | 5% |
| Gycerol | 12.5% |

ELECTROPHORESEIS CONDITIONS
50 V until samples have reached the separating gel.
100 V until the bromophenol blue runs out of the gel.
STAINING:

| | |
|---|---|
| Ethanol | 45.4% |
| Acetic Acid | 9.0% |
| Water | 45.5% |
| Coomassie Brilliant Blue | 2.5 g |

Stain overnight at room temperature with gentle shaking.
DESTAINING:

| | |
|---|---|
| Methanol | 30.0% |
| Acethic Acid | 12.5% |
| Water | 57.5% |

Destain overnight or until background is clear at room temperature.
MOLECULAR WEIGHT STANDARDS:
Low Molecular Weight Range (BRL):

| Protein | Reported MW |
|---|---|
| Insulin (A and B) | 2,300 and 3,400 |
| Bovine Trypsin Inhibitor | 5,200 |
| Lysozyme | 14,300 |
| β-Lactoglobulin | 18,400 |
| Alpha-Chymotrypsin | 25,700 |
| Ovalbumin | 43,000 |

5 ug of the protein mixture is loaded onto the SDS PAGE gel.

G.

TRYPSIN PEPTIDE MAP OF RECOMBINANT HUMAN IL-1i

PROCEDURE:

1. Reagents
   1.1 Trypsin Sequencing grade; Boehringer Mannheim GmbH.
   1.2 Urea ultra pure; BRL.
   1.3 Milli-Q water.
   1.4 Trifluoroacetic acid; Pierce.
   1.5 HPLC grade acetonitrile; J. T. Baker.
   1.6 Tris
   1.7 $CaCl_2$
2. Equipment
   2.1 HPLC system
   Beckman 114 Solvent Delivery Module
   Beckman 165 Variable Wavelength Detector
   Beckman System Gold Analog Interface Module 406
   Beckman System Gold, Personal Chromatograph Software
   2.2 Column
   BrowLee RP-300 (C8) (220 mm×4.6 mm, 7 micron)
   2.3 Heating/cooling water bath
3. Solution
   3.1 Trypsin; Dissolve 0.1 mg in 0.1 ml of 0.1 mM HCl; Store frozen at −20° C., stable for months without loss of activity.
   3.2 Urea: 8M urea in Milli Q water, make fresh daily.
   3.3 2M Tris HCl pH 8.0 and 0.1M Tris HCl pH 8.0.
   3.4 3 mM $CaCl_2$
4. Method
   4.1 Denature of IL-1i in 6M urea and 0.1M Tris pH 8.0 final concentration at about 3 mg/ml protein for 10 minutes at 37° C.
   4.2 Dilute into a solution of 0.1M Tris HCl pH 8.0 containing 0.3 mM $CaCl_2$ (1:2 vol/vol) to give a final concentration of 2M urea.
   4.3 Add trypsin solution (solution number 3.1) to give 1% by weight of the protein. Mix well.
   4.4 Incubate at 37° C. for 1 hr and additional 1% by weight of trypsin is added.
   4.5 Stop digest after an additional 3 hrs by freezing at −20° C. or by acidification with 10% trifluoroacetic acid, final concentration 0.1%.
   4.6 Inject onto the HPLC column.
5. Reverse-phase of peptide fragments produced by trypsin digestion.
   5.1 HPLC system and column as in Section 2.
   5.2 Detector settings:
   Channel A: 215 mm
   Channel B: 200 mm
   Range: 0–0.5 AU
   5.3 Mobile phase:
   A: 0.1% TFA in water
   B: 0.1% TFA in acetonitrile
   5.4 Gradient conditions

| Time (min) | Percent B | Duration |
|---|---|---|
| 0 | 0 | 0 |
| 5 | 40 | 80 |
| 85 | 100 | 5 |
| 95 | 0 | 5 |
| 120 | 0 | End |

5.5 Flow rate
1.0 ml/min
5.6 Sample preparation
none
5.7 Injection volume
50 to 100 ul H. IL-1i Bioassay The assay for IL-1 inhibitor is based on an IL-1 assay developed by S. Nakai, K. Mizuno, M. Kaneta and Y. Hirai. (*Biochem. Biophys. Res. Comm.* 154: 1189–1196. 1988). The principle of this assay is that prolonged exposure to IL-1 is cytotoxic to the human melanoma cell line A375. The cytotoxicity is mediated via the IL-1 receptor. IL-1i antagonizes this cytotoxicity in a dose dependent manner by competing with IL-1 for binding to the IL-1 receptor. The level of toxicity can be quantitated by staining the live cells with crystal violet, extracting the stain from the cells by overnight incubation in 100% ethanol, and measuring the optical density of the extracted stain with a spectrophotometer. The rationale for the use of the A375 melanoma cell bioassay is that it is a simple and direct method for measuring both IL-1 and IL-1i activity. Most other assays that have been described in the literature depend on the ability of IL-1 to activate other products, such as prostaglandin E2 and lactic acid in fibroblasts, and interleukin-2 in T-cells. These secondary products are then measured in order to determine the level of IL-1 present. Although all of these IL-1 activities are receptor mediated, the existence of more than one stage makes these alternative assays cumbersome and subject to a greater probability of error.

What is claimed is:

1. A method for the production of commercial quantities of highly purified interleukin-1 inhibitor (IL-1i), comprising:
   (1) fermentation of *Escherichia coli* comprising a plasmid containing a DNA encoding a physiologically functional interleukin-1 inhibitor (IL-1i) comprising a DNA that is selected from the group consisting of (1) a DNA that encodes IL-1i X, IL-1i alpha, or IL-1i beta and (2) a DNA (i) that cross-hybridizes to a DNA that encodes IL-1i, X, IL-1i alpha, or IL-1i beta or (ii) that cross-hybridizes to a DNA that is complementary to a DNA that encodes IL-1i X, IL-1i alpha, or IL-1i beta, wherein said DNA of (i) or (ii) encodes a protein having IL-1 inhibitor activity;
   (2) cell processing, including:
      (a) cell recovery,
      (b) lysis, and
      (c) clarification of the lysates;
   (3) a first ion exchange step using a cationic resin;
   (4) a second ion exchange step using an anionic resin;
   (5) subsequent processing steps including concentration and diafiltration.

2. The method of claim 1, wherein the cationic resin is selected from the group consisting of sulphonate cross-linked agarose-based particle matrix, sulphopropyl cross-linked dextran particle matrix, carboxymethyl cross-linked dextran particle matrix, carboxymethyl cellulose, and carboxymethyl methacrylates.

3. The method of claim 1, wherein the anionic resin is selected from the group consisting of quaternary amino cross-linked agarose-based particle matrix, diethylaminoethyl cross-linked agarose-based particle matrix, quaternary amino cross-linked dextran particle matrix, and diethylaminoethyl cellulose.

4. The method of claim 2 wherein the cationic resin is sulphonate cross-linked agarose-based particle matrix.

5. The method of claim 3 wherein the anionic resin is quaternary amino cross-linked agarose-based particle matrix.

6. The method of claim 1 which further comprises a third ion exchange step conducted immediately prior to the final processing steps.

7. The method of claim 6 wherein the third ion exchange step is conducted using a cationic resin.

8. The method of claim 7, wherein the cationic resin is selected from the group consisting of sulphonate cross-linked agarose-based particle matrix, sulphonate cross-linked dextran particle matrix, carboxymethyl cross-linked dextran particle matrix, carboxymethyl cross-linked agarose-based particle matrix, carboxymethyl cellulose, and carboxymethyl methacrylates.

9. The method of claim 8 wherein the cationic resin is sulphonate cross-linked agarose-based particle matrix.

* * * * *